United States Patent [19]
Brudnoy

[11] Patent Number: 5,825,672
[45] Date of Patent: Oct. 20, 1998

[54] METHOD AND APPARATUS FOR AUTOMATICALLY DETECTING PATTERNS IN DIGITAL POINT-ORDERED SIGNALS

[75] Inventor: David M. Brudnoy, Albany, N.Y.

[73] Assignee: The United States of America as represented by the United States Department of Energy, Washington, D.C.

[21] Appl. No.: 736,751

[22] Filed: Oct. 25, 1996

[51] Int. Cl.⁶ .......................... A61B 5/0402; G06F 17/00
[52] U.S. Cl. .......................... 364/574; 364/572; 364/417; 600/518
[58] Field of Search ................... 364/481–482, 364/485, 487, 506, 551.01, 552, 556, 572–576, 724.01; 324/76.11, 76.12, 76.47, 696, 715, 76.24, 76.15, 76.42; 600/509, 528, 546, 544, 518, 517, 521; 128/696, 732

[56] References Cited

U.S. PATENT DOCUMENTS

| | | | |
|---|---|---|---|
| 4,093,989 | 6/1978 | Flink et al. | 364/485 |
| 4,574,234 | 3/1986 | Inbar | 324/76.12 |
| 5,079,728 | 1/1992 | Adams et al. | 364/556 |
| 5,086,776 | 2/1992 | Fowler, Jr. et al. | 600/528 |
| 5,208,766 | 5/1993 | Chang et al. | 364/552 |
| 5,339,256 | 8/1994 | Levy et al. | 364/552 |
| 5,560,369 | 10/1996 | McClure et al. | 600/518 |
| 5,576,967 | 11/1996 | Grabner | 364/552 |
| 5,634,468 | 6/1997 | Platt et al. | 128/696 |

*Primary Examiner*—James P. Trammell
*Assistant Examiner*—Bryan Bui
*Attorney, Agent, or Firm*—Virginia B. Caress; William R. Moser; Paul A. Gottlieb

[57] ABSTRACT

The present invention is a method and system for detecting a physical feature of a test piece by detecting a pattern in a signal representing data from inspection of the test piece. The pattern is detected by automated additive decomposition of a digital point-ordered signal which represents the data. The present invention can properly handle a non-periodic signal. A physical parameter of the test piece is measured. A digital point-ordered signal representative of the measured physical parameter is generated. The digital point-ordered signal is decomposed into a baseline signal, a background noise signal, and a peaks/troughs signal. The peaks/troughs from the peaks/troughs signal are located and peaks/troughs information indicating the physical feature of the test piece is output.

22 Claims, 14 Drawing Sheets

METHOD AND APPARATUS FOR AUTOMATICALLY DETECTING PATTERNS IN DIGITAL POINT-ORDERED SIGNALS

The U.S. government has rights in this invention pursuant to a contract awarded by the Department of Energy.

FIELD OF THE INVENTION

The present invention relates to the field of signal processing. More particularly it relates to automatic detection of patterns in digital point-ordered signals.

BACKGROUND OF THE INVENTION

Non-invasive methods used to inspect material pieces or living matter typically involve collection of radiation from a test piece. Collected output data, as it varies with time or space, is called a signal. Of particular interest are the signal patterns (peaks and/or troughs) associated with features of interest in a test piece, which can be detected if sufficiently distinct from other competing signal shapes. An important function of signal processing is to suppress interfering signal shapes as much as possible while, at the same time, causing the patterns associated with features of interest to become more prominent visually.

One example of a non-invasive inspection method is acoustic testing. Signals collected by accelerometers attached to a machine may contain resonance peaks in the frequency spectrum of the accelerometer output signal. These peaks are indications of a possible noise source. Another example is impedance signals produced by electromagnetic probing of metallic pieces. A flaw within the metal piece will produce a distinct peak and/or trough in the impedance output signal. Identification of the peak/trough reveals the existence and location of the flaw. An example of medical monitoring is electrocardiography: certain ECG pattern anomalies indicate possible cardiac malfunctions. Yet another example is sleep-disorder testing using electrical probe output data. The appearance of certain patterns obtained by monitoring an individual during sleep may indicate physiological disorders.

Processing of signals is often performed by human analysts, who visually inspect displays or printouts of signals in search of those patterns that indicate the presence of a feature of interest. As in any process involving human judgement, however, human factors may lead to varying interpretations of the same data. Signals with low signal-to-noise ratio (SNR) values, for example, may contain patterns that appear to indicate resolvable features by some analysts but not by others. When large volumes of signal data must be inspected, particularly under tight time constraints, the likelihood of erroneous interpretation increases. For these reasons there is motivation to develop objective, automated techniques of scanning signals.

One technique for automated scanning of signals is decomposition of a point-ordered signal into additive components. The most common form of this art is the well-known linear Fourier filtering, in which a signal is linearly filtered into an equivalent spectrum in the frequency domain. The frequency interval may be divided into a number of sub-intervals of different resolution, which allows signal features of different sizes to be analyzed.

Fourier analysis, however, assumes that a signal is periodic over the entire interval of real numbers, from −infinity to +infinity. Some commonly encountered signals are non-periodic, and treating them with linear Fourier filtering obtains unsatisfactory results. A localized edge, for example, will have frequency components at all frequencies, so that the signal cannot be linearly separated along the frequency interval.

A need arises for an automated additive decomposition technique which can properly handle a non-periodic signal.

SUMMARY OF THE INVENTION

The present invention is a method and system for detecting a physical feature of a test piece by detecting a pattern in a signal representing data from inspection of the test piece. The pattern is detected by automated additive decomposition of a digital point-ordered signal which represents the data. The present invention can properly handle a non-periodic signal. A physical parameter of the test piece is measured. A digital point-ordered signal representative of the measured physical parameter is generated. The digital point-ordered signal is decomposed into a baseline signal, a background noise signal, and a peaks/troughs signal. The peaks/troughs from the peaks/troughs signal are located and peaks/troughs information indicating the physical feature of the test piece is output.

The digital point-ordered signal is decomposed by first generating a morphologically filtered signal from the digital point-ordered signal. Then a baseline signal is generated from the morphologically filtered signal. A background noise signal is then generated from the baseline signal and the digital point-ordered signal and finally, a peaks/trough signal is generated from the baseline signal, the background noise signal and the digital point-ordered signal.

DETAILED DESCRIPTION OF THE INVENTION

Figure 1:
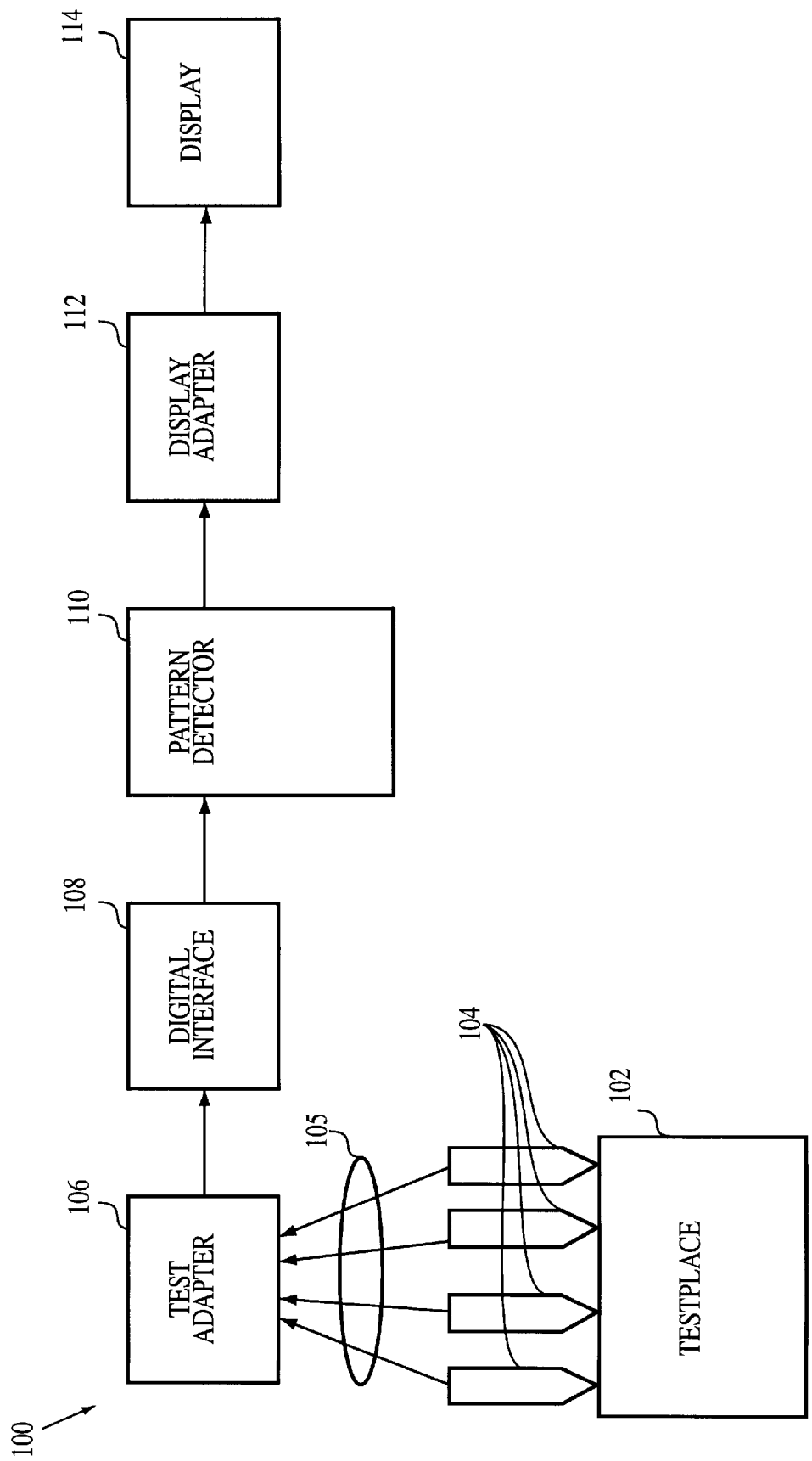
FIG. 1 is a block diagram of a test system 100 incorporating the present invention.

FIG. 1 is a block diagram of an exemplary test system 100 incorporating the present invention. Test piece 102 may be any item which is under test. Test probes or transducers 104 provide the initial signal output 105 from the test. Signal 105 is one or more signals which are representative of physical properties of the test piece. For example, test piece 102 may be a machine which is undergoing acoustic testing and probes 104 are accelerometers which provide output signals 105 representative of the acceleration present at various locations on the machine. Test piece 102 may be a metallic piece which is undergoing electromagnetic probing and probes 104 are electromagnetic probes which provide output signals 105 which are representative of probe impedances at various portions of the metallic piece. Test piece 102 may be a living organism, such as, for example, a human subject or a test animal and probes 104 may be electrocardiogram probes which output signals 105 which are representative of electrical activity of the heart of the human subject or test animal 102. Although these specific embodiments have been described, test piece 102 may be any item on which measurements may be performed and probes 104 may be any measuring device which generates an output signal 105 representative of the property being measured.

Probes 104 are connected to test adapter 106, which accepts signals 105 as inputs. Test adapter 106 contains circuitry which provides the necessary signal processing, such as, for example, amplification, buffering or frequency filtering, to adapt the input signals for digitization. Test adapter 106 may also provide power and/or control signals to probes 104 in order to control the testing and cause it to be properly performed. The details of test adapter 106 depend upon the testing being performed, but, for all well-known tests, these details are well-known. The processed signals are output to digital interface 108. Digital interface 108 contains analog to digital converters (ADCs). As is well-known, ADCs convert analog electrical signals into digital electrical signals representative of the amplitude of the analog electrical signals. Digital interface 108 also contains circuitry to interface the digital electrical signals to pattern detector 110. Pattern detector 110 may be a programmed general purpose digital computer, such as, for example, a personal computer, a workstation, a minicomputer or a mainframe. Pattern detector 110 may also be a dedicated special purpose digital computer or it may be dedicated hardware. Pattern detector 110 generates output signals representative of the patterns which it has detected in the input signals. These output signals are input to display adapter 112 which provides them to display 114.

Figure 2:
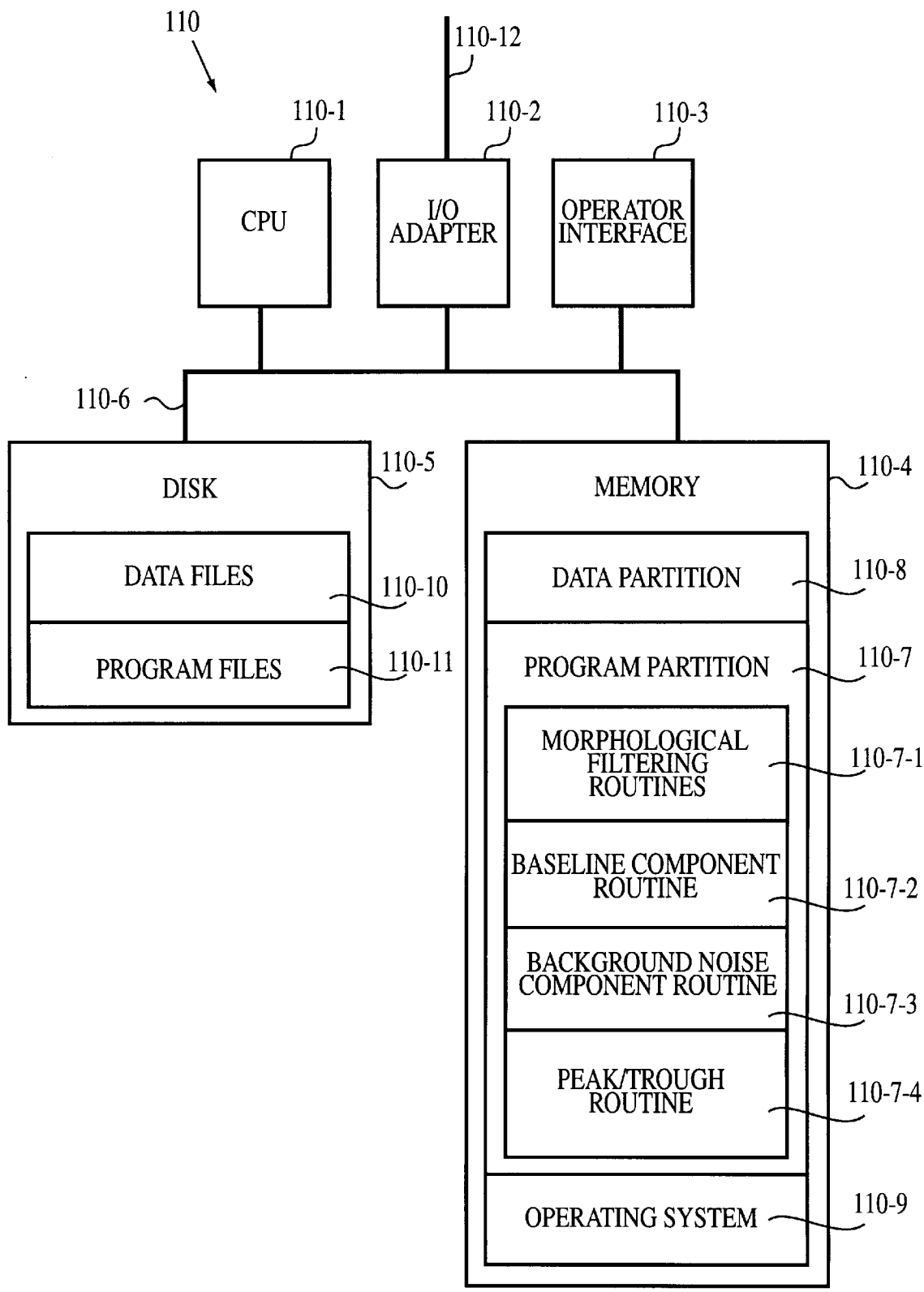
FIG. 2 is a block diagram of one embodiment of a pattern detector 110 of test system 100, as shown in FIG. 1.

FIG. 2 is an exemplary block diagram of one embodiment of a pattern detector 110, as implemented by a programmed computer. Pattern detector 110 includes a CPU 110-1, for executing program instructions and processing data, memory 110-4, for storing program instructions executed by and data processed by CPU 110-1, disk storage 110-5, for storing programs and data to be transferred to and from memory, and at least one I/O adapter 110-2, for communicating with other devices and transferring data in and out of the computer system over connection 110-12. Pattern detector 110 may also include an operator interface 110-3, for providing status information to and accepting commands from a system operator. All these elements are interconnected by bus 110-6, which allows data to be intercommunicated between the elements. I/O adapter 110-2 represents one or more I/O adapters or network interfaces which connects pattern detector 110 to digital interface 108 and display adapter 112 over connection 110-12.

Memory 110-4 is accessible by CPU 110-1 over bus 110-6 and includes operating system 110-9, program partition 110-7 and data partition 110-8. Program partition 110-7 stores and allows execution by CPU 110-1 of program instructions which implement the NLAD process. Program partition 110-7 includes morphological filtering routines 110-7-1, baseline signal component construction routine 110-7-2, background noise component construction routine 110-7-3 and peak/trough component construction routine 110-7-4. Data partition 110-8 is accessible by CPU 110-1 and stores data used during the execution of program instructions. In particular, data representing the signal being processed is stored in data partition 110-8. Disk 110-5 contains program files 110-11, which store the programs for transfer to memory 110-4 and data files 110-10, which store data for transfer to or from memory 110-4.

Figure 3:
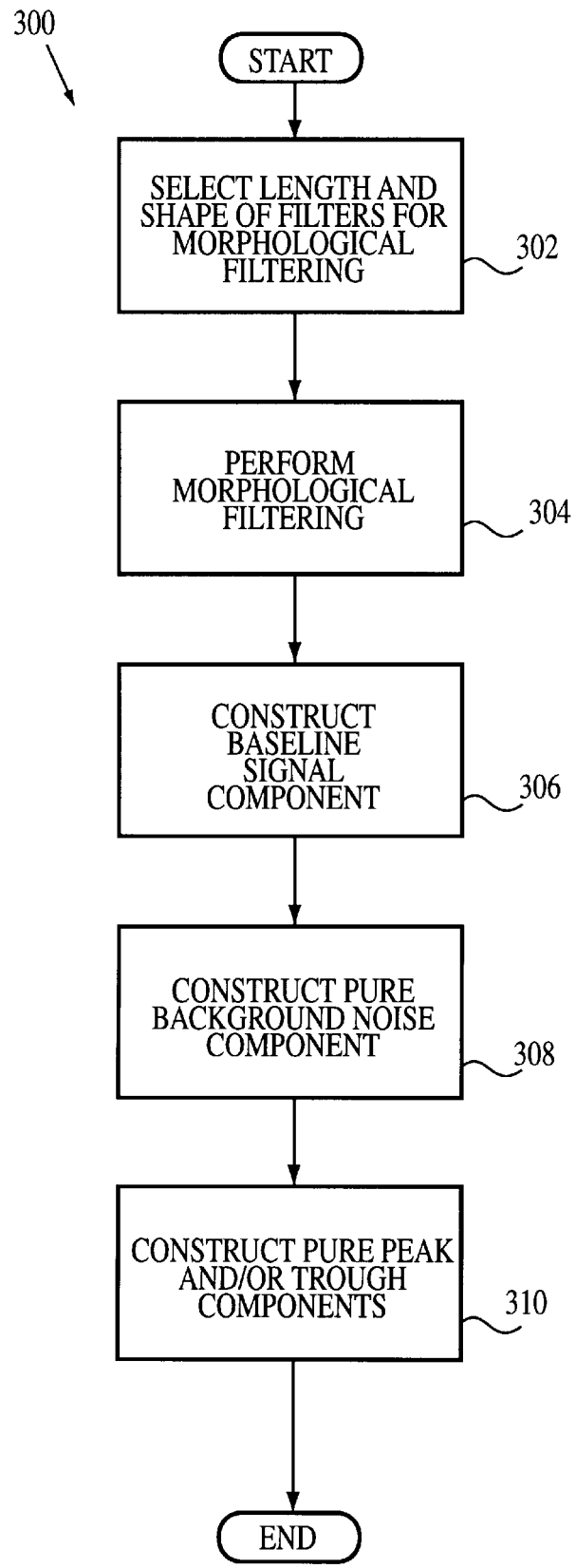
FIG. 3 is a flow diagram of a process 300 performed by test system 100, in accordance with the present invention.

FIG. 3 is a block diagram of a non-linear additive decomposition (NLAD) process 300. Process 300 begins with step 302, in which the length and shape of the filters to be used in the morphological filtering, step 304, are selected. The filter length should be selected to be no smaller than the width of the widest signal pattern which is to be detected. The shape of the filter selected is typically flat. This is known as a line filter. Other shapes, such as Gaussian, etc. may be selected. This is described in detail below. In step 304, morphological filtering is applied to the signal. In step 306, a baseline signal component is constructed from the output signals of the morphological filtering. In step 308, a pure background noise component signal is constructed from the signal, the baseline signal component and the morphological filtering signals. In step 310, a pure peak and/or trough component signal is constructed from the signal, the baseline signal component, the background noise component signal and the morphological filtering signals. It is apparent that the steps of process 300 must be performed in this order, because the background noise component is defined with respect to the baseline component and the peaks/troughs component is defined with respect to both the baseline and background noise components.

The following symbols are defined to represent a signal and its components:

signal ... S baseline component ... $S_{baseline}$ background noise component ... $S_{noise}$ peaks/troughs component ... $S_{p/t}$ The non-linear additive decomposition is expressed as $$S = S_{baseline} + S_{noise} + S_{p/t}$$

Figure 4:
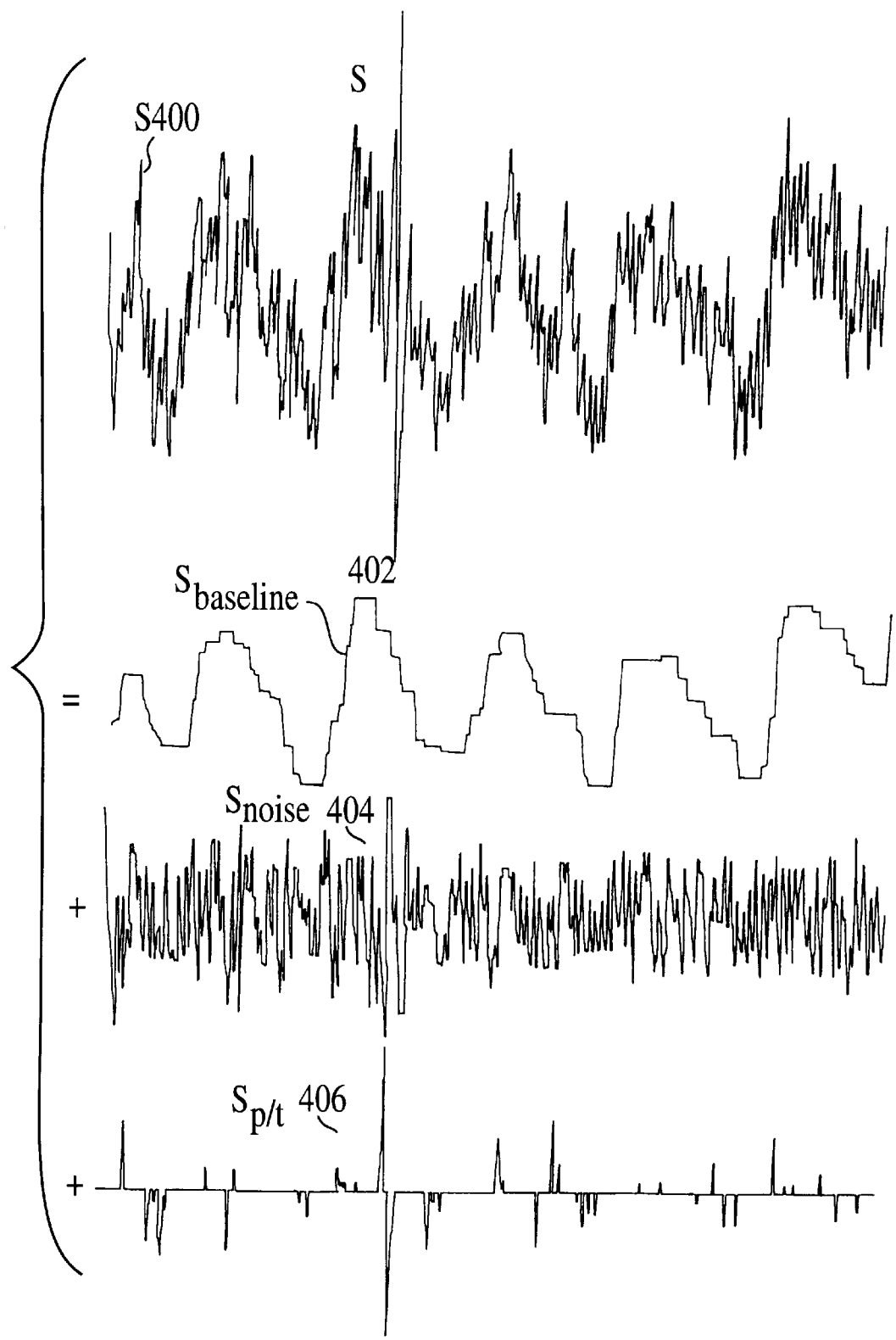
FIG. 4 is a graphical representation of the additive decomposition of a signal S into its components $S_{baseline}$, $S_{noise}$ and $S_{p/t}$.

A graphical example of this algebraic representation of NLAD is found in FIG. 4, which shows a noisy signal, S 400, exhibiting overall sinusoidal behavior, with a few possible peaks/troughs. After decomposition, each component manifests distinct resolution scale information:

$S_{baseline}$ 402 displays overall sinusoidal form;

$S_{noise}$ 404 displays random fluctuations;

$S_{p/t}$ 406 displays peaks and troughs.

FIG. 4 illustrates NLAD processing of a signal containing both random-appearing noise and undulatory-appearing overall behavior. Each component of the signal contains resolution scale information distinct from that of the other two components. Peaks and troughs, for example, may be picked out of $S_{p/t}$ unencumbered by any significant contribution of noise. Similarly, local noise level may be obtained from $S_{noise}$ with no concern that large peaks or troughs will mistakenly contribute large values to that level. Overall behavior is obtainable from $S_{baseline}$ with no contamination from signal effects at lesser resolution scales.

It is the (automatic) detection of the latter peaks and troughs that is one of the important objectives of signal processing. In many applications, resolution size is chosen so that the peak/trough component exhibits the signal patterns that represent the test piece features of interest. As is well known, an automated peak location method may be applied to the $S_{p/t}$ component to derive peak positions in the signal, thereby automating the entire data processing operation, from start to finish. In some cases peak position can be correlated with test piece location, so that feature location is identified automatically, as well.

The background noise component, calculated adaptively, provides a local value of noise; therefore the computed signal-to-noise ratio (SNR) for any detected feature is based on local—not external—quantities. A minimum value for SNR determines whether or not the detected feature is accepted as a significant feature. The minimum SNR value for acceptance may be chosen for each application, at the discretion of each testing group. This flexibility is another feature of this invention.

The baseline signal component, which displays signal variation at coarse resolution, performs an additional important function. The calibrated null value of a signal may drift over a broad signal region, sometimes due to equipment performance. The drift appears in the baseline signal component only, since it is a coarse resolution phenomenon. When peak/trough indications are obtained from the intermediate resolution, or peaks/troughs, component, drift behavior will not be mis-identified as a peak/trough. Consequently reliability of the method is increased as well as confidence in the processed results.

A. Overview of NLAD

The present invention automates the detection of signal patterns by emulating two important characteristics of human visual skills, (1) global perception, and (2) reasoning with shapes, to visually separate out details at different scales of resolution. Global perception means than an entire signal, or signal section, is treated as the fundamental object of processing. Reasoning with shapes means that signals are analyzed by considering their geometric shape rather than their quantitative behavior. This approach is appropriate for automating visual signal inspection because it is a visual emulation applied to what is fundamentally a visual task. Since the appropriate tools are applied to the task, the process created is more robust and reliable in practice.

Vision emulation for purposes of detecting signal patterns is based on methods taken from the image processing field of mathematical morphology. These methods are designed to process signals (and other images) by filtering them with geometric filters. By choosing appropriate sequences of filtering, and by selecting appropriate filters and filter sizes, specific information concerning signal patterns is extracted. These morphological filtering sequences may be viewed as the practical implementation of the concept of global perception using visual shape-reasoning.

Suppression of unwanted detail is one of the important goals of any signal processing technique. In this invention this goal is achieved, i.e., signal patterns (peaks and/or troughs) are identified in the presence of signal noise, and in the presence of competing—but visually distinguishable—signal patterns, through methods that emulate the human capability of visual separation. The term "visual separation" means that a human observer can separate out and suppress details in an image that are at higher ("finer") and lower ("coarser") levels of resolution than those at any selected reference scale of resolution.

Central to the method of this invention is the decomposition of a signal into three mutually distinct components, based on "coarse", "fine", and "intermediate" levels of visual resolution. Resolution selection is emulated by choosing a filter size, or sizes, in order to decompose a signal into components by appropriate sequences of morphological operations. The morphological operations emulate two important human skills necessary for visual separation, global perception and reasoning with shapes. The result of decomposition is a disentanglement of resolution information contained in a signal so that the contribution from each grouping can be viewed separately. Emulation of the human capability of visual separation for signal processing is novel to this method.

The coarsely resolved signal component, here called the "baseline component", is sensitive only to overall, low resolution, signal behavior. It does not display rapid variation (high resolution features, often associated with random noise) nor does it display moderate variation (intermediate resolution features, which may include visually prominent peaks or troughs).

The finely resolved signal component, here called the "background noise component", is chosen to be sensitive only to signal variation at high resolution. No overall signal behavior is manifested by this component nor does it display signal variation at an intermediate range of resolution.

The intermediate signal component is what remains after baseline behavior and background noise are removed from the signal. It is a particularly simple component to construct because, even through the decomposition is performed by morphological operations that are inherently non-linear, the components themselves combine additively. This means that the intermediate component is obtained by arithmetic subtraction of the baseline plus background noise components from the signal. In many applications resolution range is chosen so that the peaks and/or troughs that represent features of interest are contained only in the intermediate resolution component. Signal decomposition, then, provides a means by which the presence of features of interest may be detected almost completely free of other, interfering, signal features.

Non-linear additive decomposition (abbreviated, NLAD), as this method of signal decomposition has been named, can be implemented automatically by computer. Furthermore, for many testing applications, resolution range is best provided by quantities obtained from the testing system itself. In these cases signal processing is performed autonomously (using only internal testing system information) as well as automatically. Only the point-ordered digital signals, specified sizes of relevant test piece structures, and resolution capabilities of the measuring devices need to be provided. All other relevant information is derived adaptively during the process of decomposition, based entirely on operations that emulate the way a human analyst would perform the same visual tasks. The complete autonomy that is possible with NLAD processing creates greater reliability in the method's application and confidence in the results it produces.

B. Morphological Filtering

1. Description of Morphological Filtering Operations

A morphological "open" filtering of a signal with a line filter is a smoothing operation that filters out peaks of widths less than the length of the filter. In this context "width" is not defined precisely, but is associated with the size of the peak/trough near its base. After open filtering, peaks of appropriate width and smaller are all removed, but troughs of all widths remain. Morphological filtering is described in greater detail below.

A morphological "close" filtering of a signal with a line filter is another smoothing operation that filters out troughs of widths less than the length of the filter; however, peaks of all widths remain. Close filtering may be viewed as a type of "mirror imaging" of open filtering, in the sense that troughs and peaks can be viewed as mirror images of each other.

Figure 5:
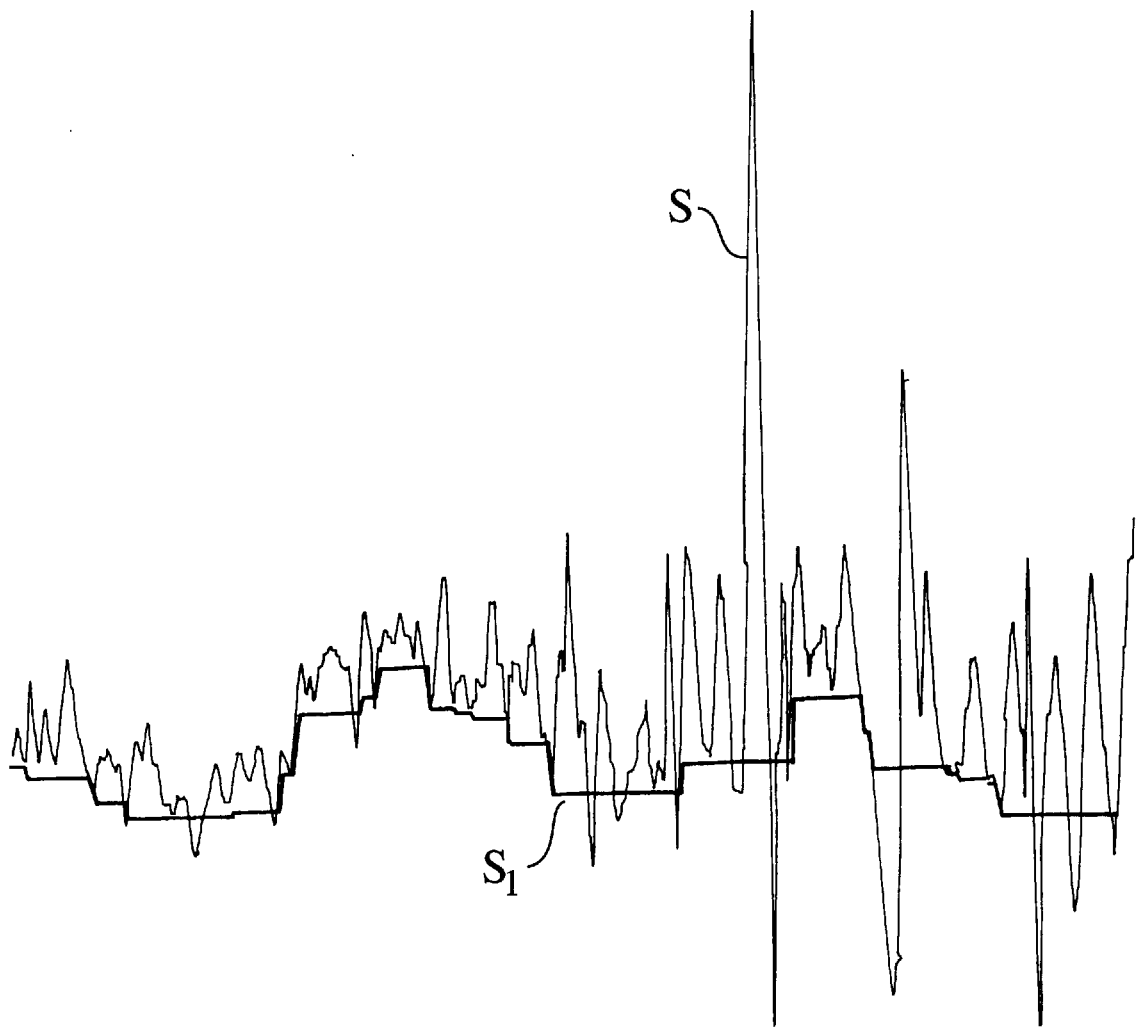
FIG. 5 is a graphical representation of a lower bound envelope signal, $S_l$, resulting from morphological filtering of a signal.
Figure 6:
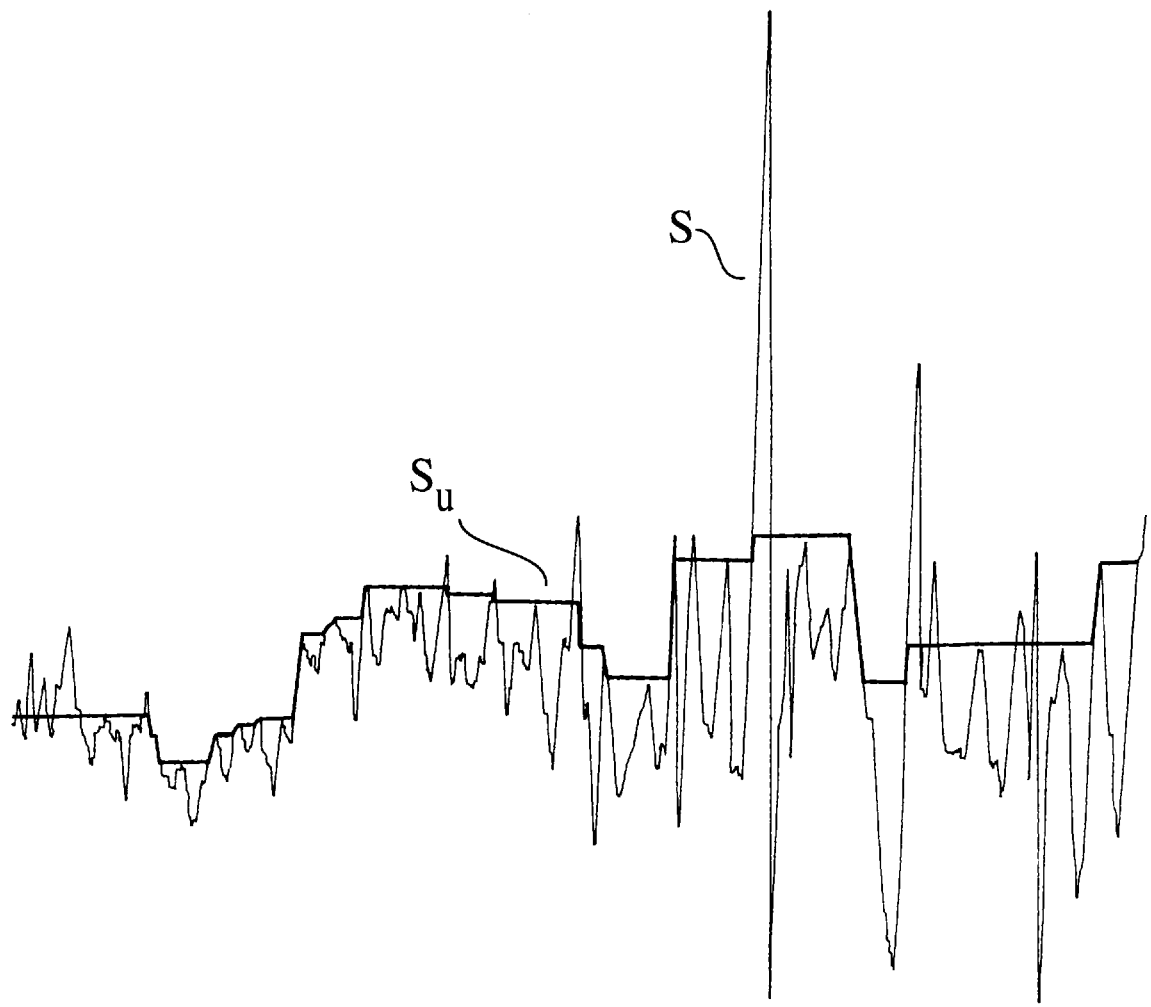
FIG. 6 is a graphical representation of an upper bound envelope signal, $S_u$, resulting from morphological filtering of a signal.

To remove both peaks and troughs, either one of two-sequence filtering operations can be performed: a) open filtering followed by close filtering of the open-filtered signal, or b) close filtering followed by open filtering of the close-filtered signal. The sizes of the filters used in either one of the two-sequence processes need not be the same, so that peaks of one width and smaller are removed together with troughs of another width and smaller. The open-then-close sequence operation produces a lower bound envelope to the signal except in regions containing troughs of appropriate widths; in these regions the filtered signal cuts through troughs (the longer the close-filter size is compared to trough width, the nearer to the trough base the resulting filtered signal will appear). Likewise, the close-then-open sequence produces an upper bound envelope to the signal except in regions containing peaks of appropriate widths; in these regions the filtered signal cuts through peaks (the longer the open-filter size is compared to peak width, the nearer to the peak base the resulting filtered signal will appear). The "lower bound" signal is designated $S_l$ and the "upper bound" signal is designated $S_u$. An example of $S_l$ construction is given in FIG. 5; similarly, $S_u$ construction is given in FIG. 6.

2. Morphological "Open" and "Close"

Morphological Open is defined in terms of two simpler morphological operations, "erode" and "dilate", as follows:

Signal {S} and filter {g}:

| | |
|---|---|
| Erode (S,g)[n] = | min{S(n+j) − g(j)},<br>j<br>j defined wherever {g} is defined. |
| Dilate (S,g)[n] = | max{S(n−j) + g(j)},<br>j<br>j defined wherever {g} is defined. |

The operation Erode decreases the shapes of signal {S} using {g} as a shape template. Similarly, the operation Dilate increases the shape of signal {S} using {g} as a shape template.

For line filters the value of {g} is 0.0 wherever {g} is defined.

The "open" operation is the two-sequence "first-erode-then-dilate":

Open(S,g)[n]=Dilate(Erode(S,g),g)[n].

The "close" operation is the dual of "open", i.e.,

Close(S,g)[n]=−Open(−S,−g)[n].

The open-filtered signal, {Open(S,g)}, bounds {S} from below at every datum point, while producing a smoothed, approximate version of {S} at a resolution scale defined by {g}. Similarly, the close-filtered signal, {Close(S,g)}, bounds {S} from above at every datum point, while producing a smoothed, approximate version of {S} at a resolution scale defined by {g}.

C. Construction of the Baseline Component

When an open-then-close sequence of filtering is performed on S, using a line filter of size '$n_f(1)$' for the open filtering and a line filter of size '$n_f(2)$' for the close filtering, a "lower bound" signal is constructed, as described above. Coarse resolution of the twice-filtered signal is guaranteed if the lengths of the filters are chosen to be no smaller than the width of the widest signal pattern to be detected. Similarly, if a close-then-open sequence of filtering is performed on S, using a line filter of size '$n_f(1)$' for the close filtering and a line filter of size '$n_f(2)$' for the open filtering, then an "upper bound" signal is constructed.

Figure 7:
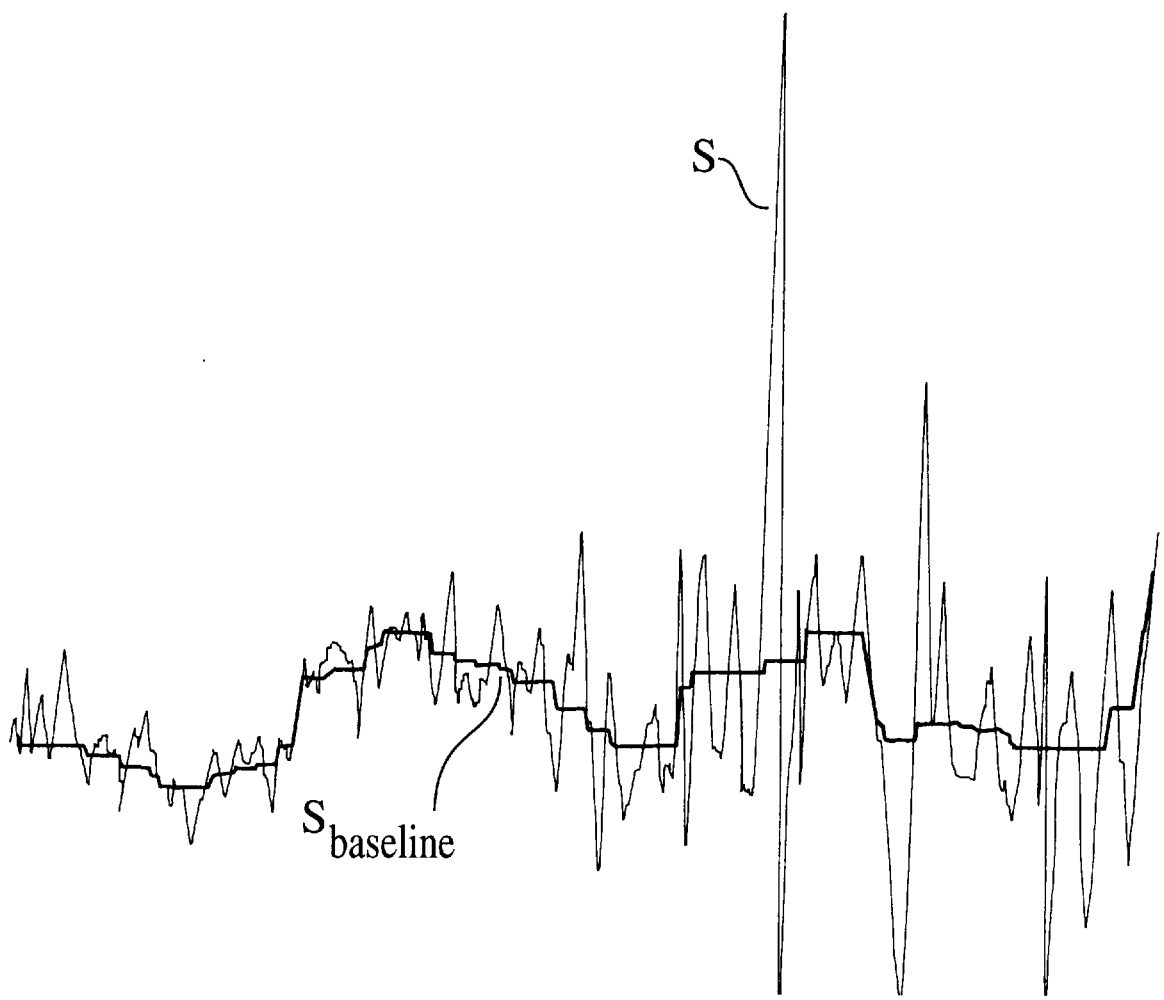
FIG. 7 is a graphical representation of the baseline component, $S_{baseline}$, of a signal, S.

The baseline signal, $S_{baseline}$, is constructed from the two bounding signals, as follows:

$$S_{baseline}=(S_u+S_l)/2,$$

where $S_u$ and $S_l$ are described above. $S_{baseline}$, then, follows the signal half-way between its lower and upper coarsely resolved bounds. Either one of the three constructions, $S_u$, $S_l$, or one-half of the sum of the bounding values, may serve equally well as the coarse component of the signal, because each follows the signal's overall behavior and each is insensitive to background noise, peaks and troughs. Choice of the lower bound means that all values of the background noise component, defined below, are positive. Similarly, choosing the upper bound means that all values of background noise are negative. The choice of $S_{baseline}$, given above, means that background noise may take on both positive and negative values. FIG. 7 shows the baseline component of the signals of FIGS. 5 and 6.

D. Construction of the Background Noise Component

Background signal noise is defined in non-peak and non-trough regions as small amplitude behavior with respect to the baseline. Small amplitude is defined operationally: whenever the signal's value falls between the upper and lower bounds, as constructed in section B, then the signal's amplitude, with respect to the baseline, is small. In the peak regions, background noise is defined as the difference between the upper bound and the baseline component; similarly in the trough regions. Specifically, $$S_{noise} = S - S_{baseline}, \quad S_l \leq S \leq S_u$$
(non-peak, non-trough region)
$$= S_u - S_{baseline}, \quad S \geq S_u$$
(peak region)
$$= S_l - S_{baseline}, \quad S \leq S_l$$
(trough region)

Figure 8:
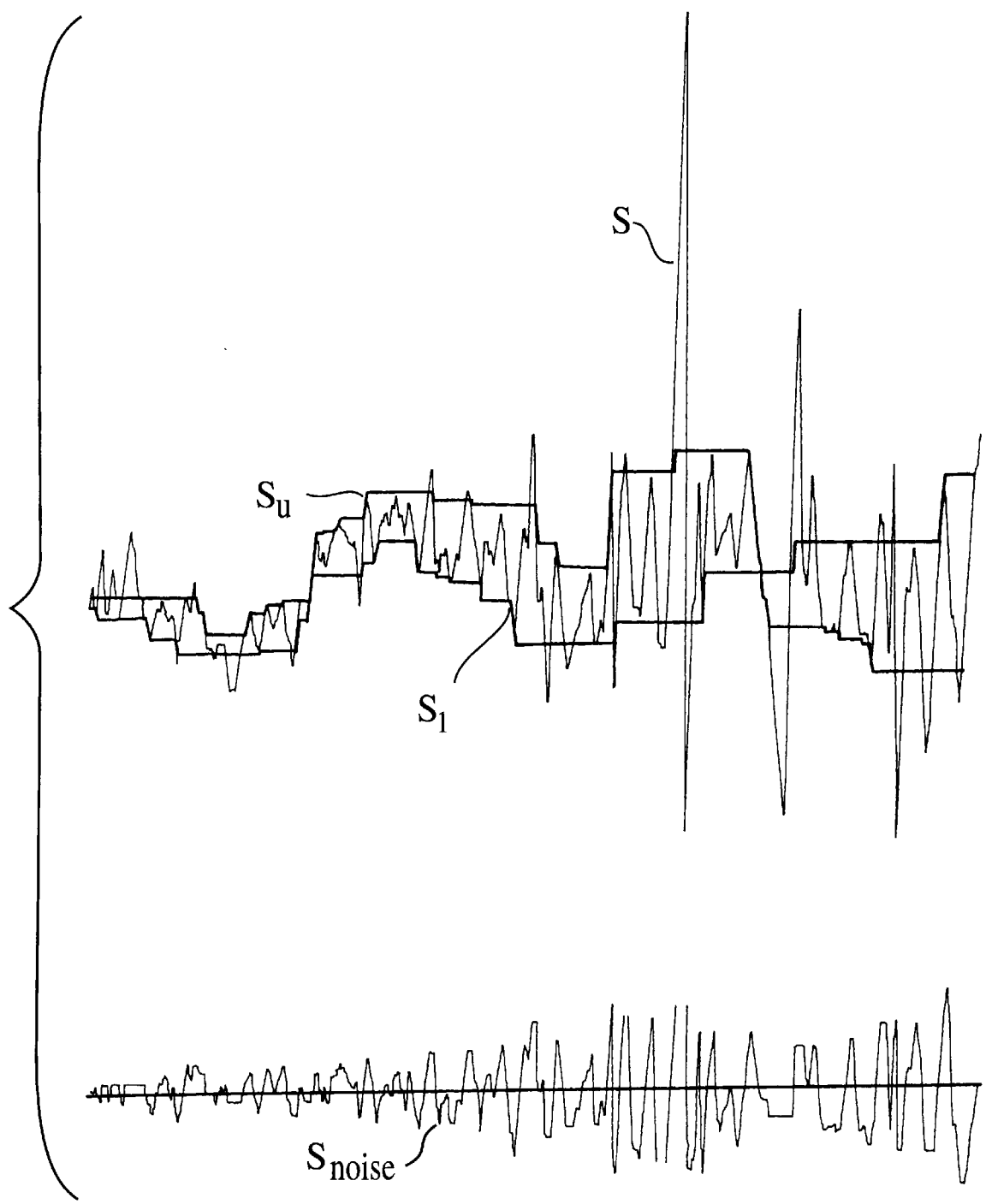
FIG. 8 is a graphical representation of the background noise component, $S_{noise}$, of a signal, S, and the "upper" and "lower" bound signals used to construct $S_{noise}$.

FIG. 8 illustrates the construction of a background noise component signal, $S_{noise}$.

In this manner signal noise is defined at all data points, and, consequently, a measure of noise over any signal interval can be obtained from signal data only. The precise definition of the quantity "measure of noise" is left to the choice of each testing group, since noise-magnitude may be provided in a variety of ways. For example, the root-mean-square of $S_{noise}$ is one measure of noise; the maximum-to-minimum value of $S_{noise}$ is another. A parameter such as one of these may be used as noise-magnitude for computing signal-to-noise-ratio (SNR). This adaptive and flexible method for assessing the noise content in a signal is a novel feature of NLAD signal processing.

E. Construction of Peaks/Troughs Component

According to sections C and D, the signal in all non-peak and non-trough regions is an additive sum of the baseline and background noise components. Subtracting the baseline and background noise components from the signal everywhere produces a signal component exhibiting isolated peaks and troughs on a zero base, i.e., $$S_{p/t} = S - S_{baseline} - S_{noise}$$
$$= 0, \quad S_1 \leq S \leq S_u$$
(non-peak, non-trough region)
$$= S - S_u, \quad S \geq S_u$$
(peak region)
$$= S - S_1, \quad S \leq S_1$$
(trough region)

Figure 9:
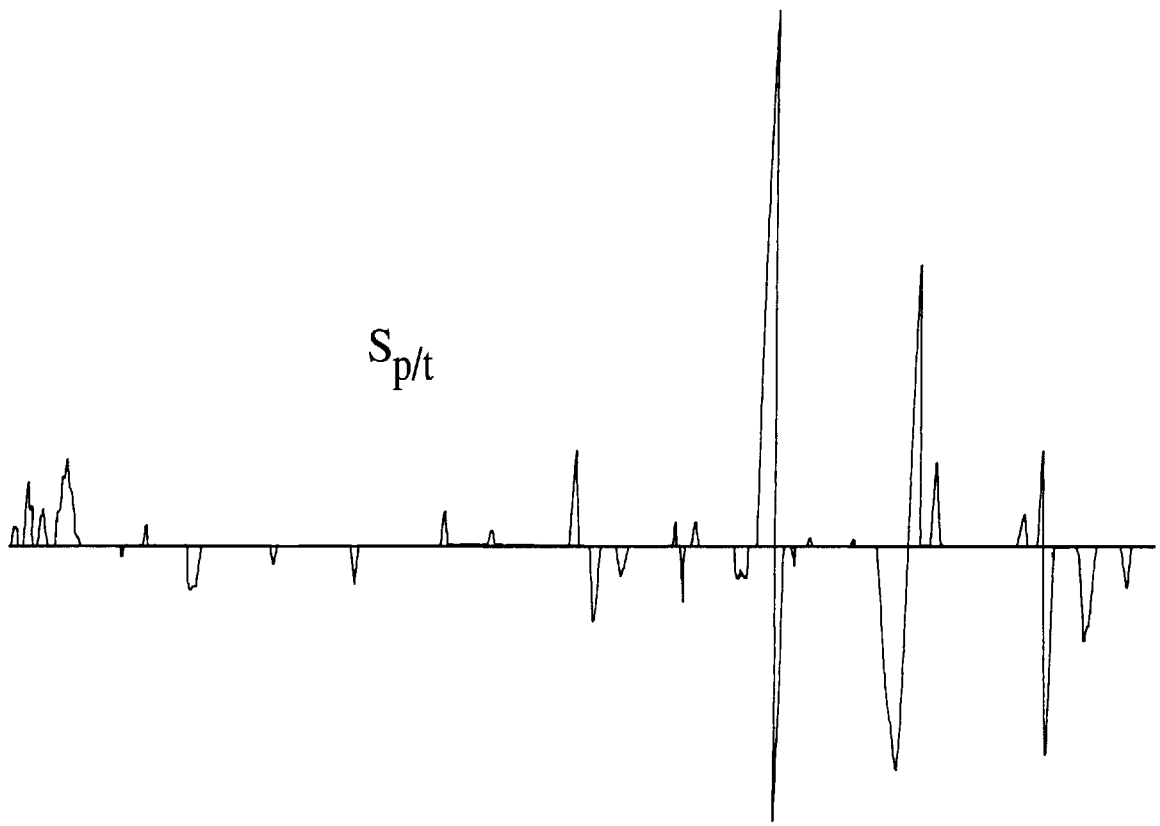
FIG. 9 is a graphical representation of the peaks/troughs component, $S_{p/t}$, of a signal, S.

FIG. 9 illustrates the construction of $S_{p/t}$.

A peaks-only component is obtained from $S_{p/t}$ by adding $S_{p/t}$ to the absolute value of $S_{p/t}$: $[S_{p/t}+[S<]\inf p/t[[M]]]$; a troughs-only component is obtained by subtracting the absolute value of $S_{p/t}$ from $S_{p/t}$: $[S_{p/t}-S_{p/t}[[M]]]$. This construction is possible because the peaks/troughs component is guaranteed to have a zero base.

Almost all signal features that could interfere with the identification of a peak or trough in a signal have been removed from the peaks/troughs component, leaving $S_{p/t}$ exceptionally "clean". Any peak or trough will have a well-defined height or depth that is compared to local noise-magnitude to obtain a SNR value.

F. Extensions

1. Multiple Applications of NLAD

A peaks/troughs component constructed at one level of resolution may be further decomposed at a finer level of resolution. Likewise, the resulting peaks/troughs component constructed by the second NLAD may be further decomposed at an even finer level of resolution; and so on, to the limits of practical resolution. The capability of viewing and re-viewing an image at different levels of resolution is a well-recognized human visual skill, emulated in this invention by multiple application of the NLAD process.

Figure 10A:
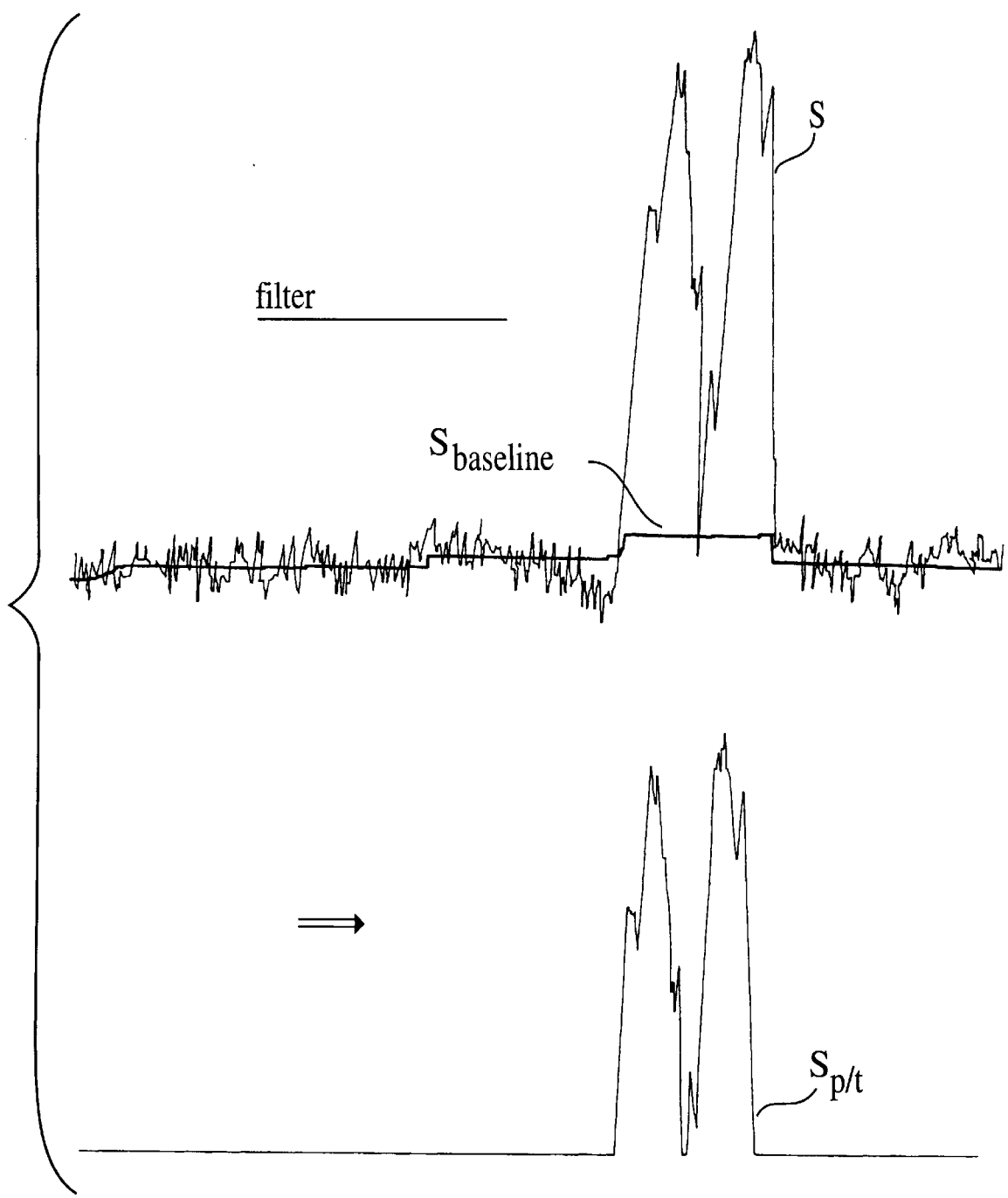
FIG. 10a is a graphical representation of the peaks/troughs component (bottom) of a signal (top) after decomposition at filter length shown.
Figure 10B:
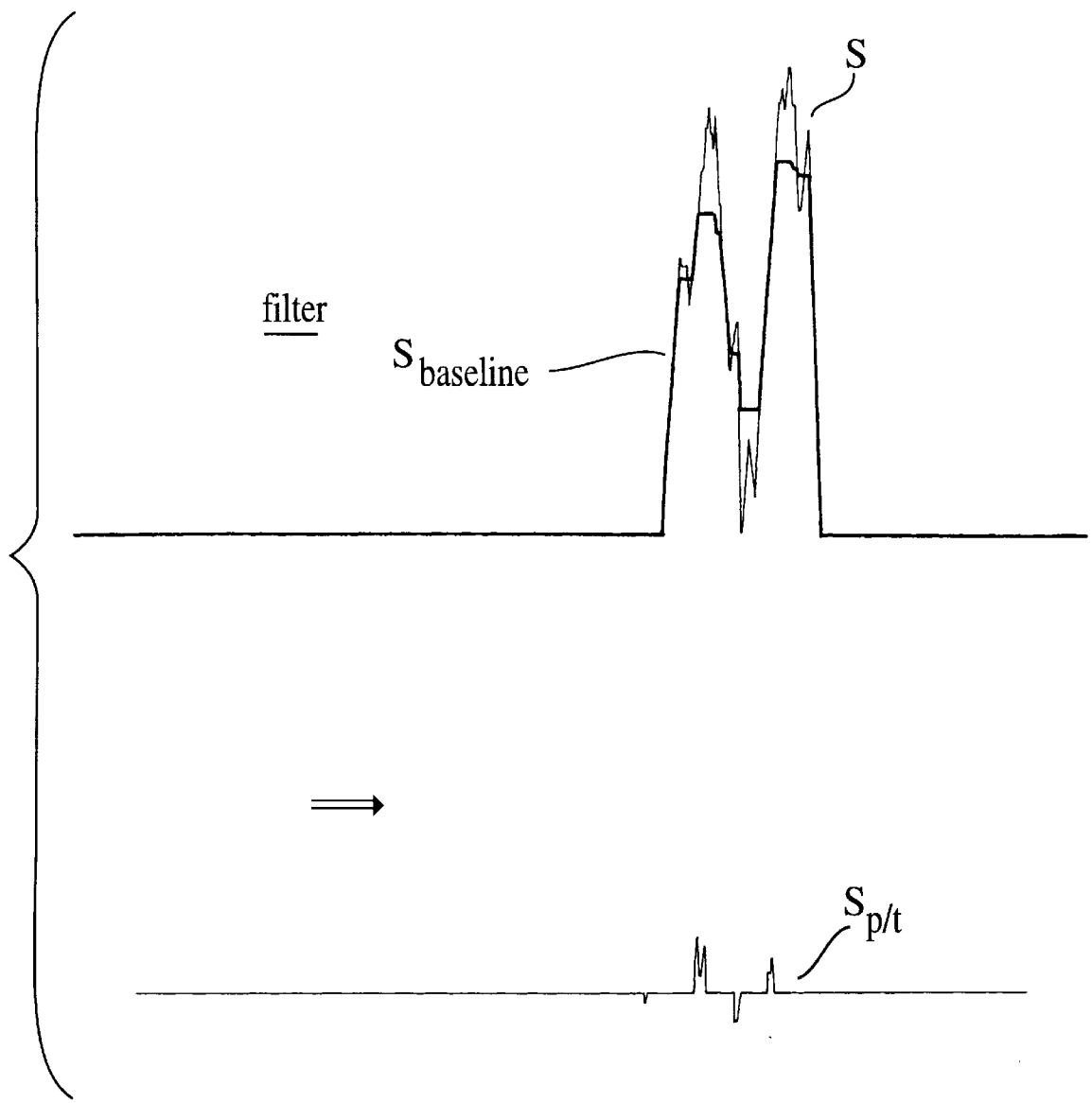
FIG. 10b is a graphical representation of peaks/troughs component (bottom) of the peaks/troughs component of FIG. 10a (top) after a second decomposition at filter length 1/10 that of the first filter.

FIGS. 10a and 10b demonstrate two successive NLAD operations, the second operation performed at 1/10 the resolution scale of the first NLAD operation. Detail not resolved after the first decomposition is resolved after the second.

2. Graytone NLAD

Instead of performing NLAD with line filters, the same sequence of operations may be performed with graytone filters in order to produce a graytone three-component decomposition. Differences in the implementation and interpretation of component contents may appear.

The morphological operations of open and close are known in the art as operations that are "dual" to each other. An example of what this means for signals is as follows. Open-filter a signal with a graytone filter of any shape. Rotate the original signal 180-degrees about an axis through the origin and perpendicular to the signal plane. "Close-filter" the rotated signal with the same graytone filter shape as before, with the filter shape rotated 180-degrees about the origin. Rotate the close-filtered signal another 180-degrees about the origin. The open-filtered signal and the [rotated=>close-filtered=>rotated]-signal are identical. What this means for graytone-NLAD is that if the graytone filter for morphological opening is {g(n)}, then the graytone filter for morphological closing is {-g(-n)}.

Figure 11A:
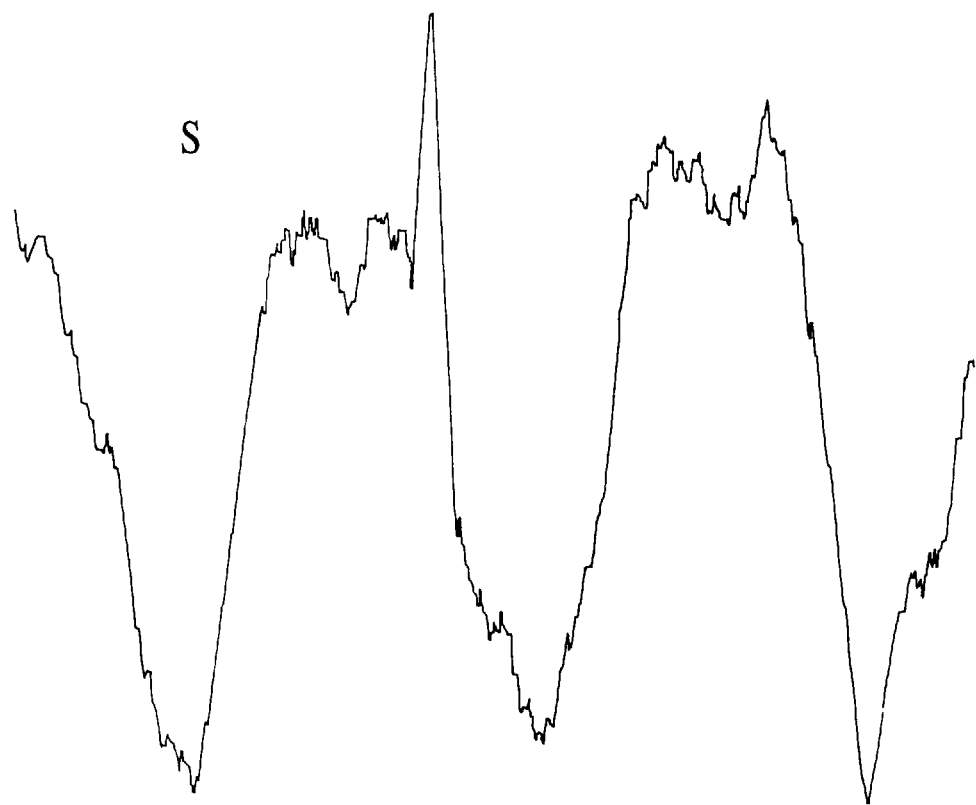
FIG. 11a is a graphical representation of a signal, S.
Figure 11B:
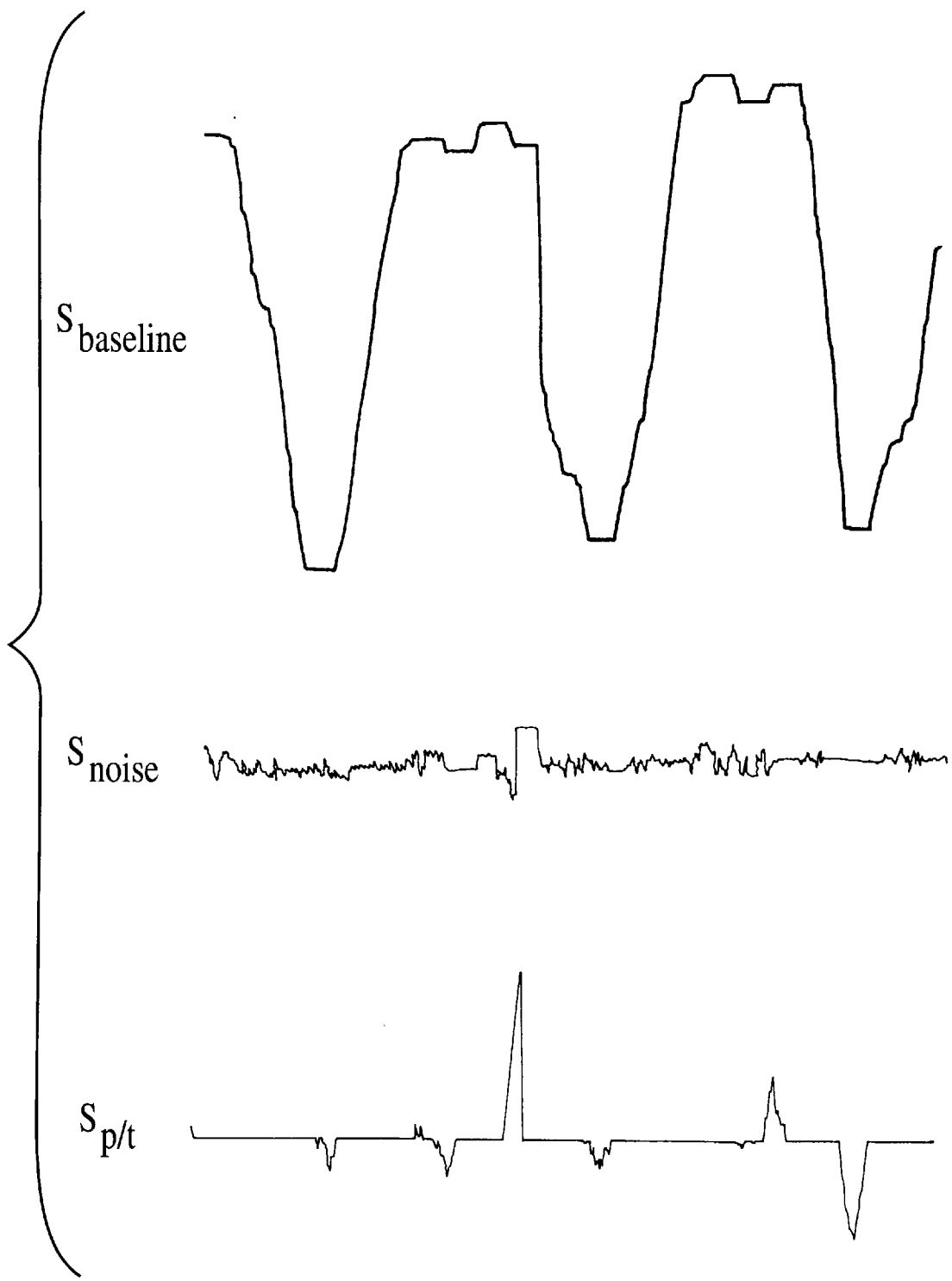
FIG. 11b is a graphical representation of the signal, S, of FIG. 11a after NLAD filtering with a line filter.
Figure 11C:
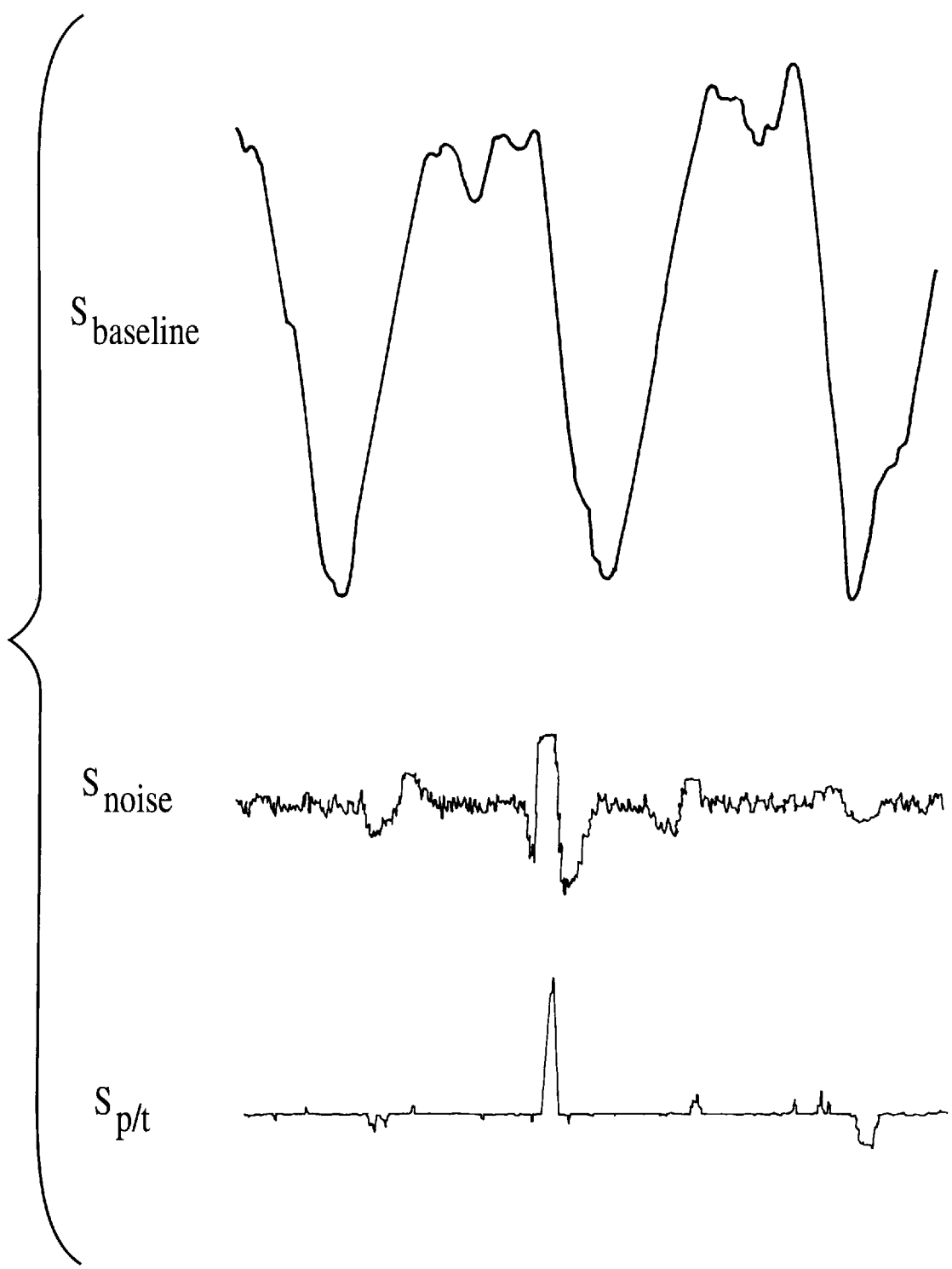
FIG. 11c is a graphical representation of the signal, S, of FIG. 11a after NLAD filtering with graytone filter having a Gaussian characteristic.

Graytone NLAD includes not only relative resolution information, as previously described, but also shape information. For example, if the graytone filter is a Gaussian with finite edges, the graytone baseline component can contain signal peaks or troughs that, in the case of line filter decomposition, were included in the peaks/troughs component. FIGS. 11a–11c show a graytone NLAD (Gaussian filter) together with a NLAD of the same signal using a line filter whose length equals 1/3 the base of the Gaussian. FIG. 11a is the signal, which exhibits random noise, undulatory baseline behavior, and contains a prominent peak about midway along the signal. FIG. 11b is a NLAD of the signal in FIG. 11a using a line filter. The prominent peak shows up in the peaks/troughs component of the decomposition. FIG. 11c is the graytone NLAD of the same signal. The prominent peak shows up in this peaks/troughs component, as well, but smaller peaks, displayed in the $S_{p/t}$ component of FIG. 11b are included in the baseline component, $S_{baseline}$, of FIG. 11c. Note that, in general, the baseline component of the graytone NLAD appears smoother with a Gaussian graytone filter than the comparable component of the line filter NLAD.

It may be understood by those of ordinary skill in the art that further variations and modifications can be effected within the scope of the invention. The method may be extended to any application in which automatic scanning of digital, point-ordered signals is needed to identify signal patterns.

What is claimed is:

1. An automated, computer-implemented method for detecting signal information representing a physical feature of a test piece by detecting a pattern in a signal representing data from inspection of the test piece, comprising the steps of:

measuring a physical parameter of the test piece;

generating a digital point-ordered signal representative of the measured physical parameter;

decomposing the digital point-ordered signal into three components, based on resolution, comprising a coarse resolution baseline signal, a fine resolution background noise signal, and an intermediate resolution peaks/troughs signal;

locating peaks/troughs from the peaks/troughs signal; and outputting peaks/troughs information identifying those signal patterns that indicate the presence of physical features of the test piece.

2. The method of claim 1, wherein the test piece is a mechanical object and the measured physical parameter is the acceleration measured at a location on the mechanical object.

3. The method of claim 1, wherein the test piece is a metallic piece and the measured physical parameter is the impedance produced by electromagnetic probing of the metallic piece.

4. The method of claim 1, wherein the test piece is a living organism and the measured physical parameter is the electrical activity within the living organism.

5. The method of claim 1, wherein the decomposing step comprises the steps of:

generating a morphologically filtered signal from the digital point-ordered signal;

generating a baseline signal from the morphologically filtered signal;

generating a background noise signal from the baseline signal and the digital point-ordered signal; and generating a peaks/trough signal from the baseline signal, the background noise signal and the digital point-ordered signal.

6. The method of claim 5, wherein the baseline signal comprises coarse resolution behavior of the digital point-ordered signal relative to the background noise signal and the peaks/troughs signal.

7. The method of claim 5, wherein the background noise signal comprises fine resolution behavior of the digital point-ordered signal relative to the baseline signal and the peaks/troughs signal.

8. The method of claim 5, wherein the peaks/troughs signal comprises intermediate resolution behavior of the digital point-ordered signal relative to the baseline signal and the background noise signal.

9. The method of claim 8, wherein the decomposing step is performed at a first resolution level and the method further comprises the step of:

decomposing the peaks/troughs signal constructed at the first resolution level into a baseline signal, a background noise signal, and a peaks/troughs signal constructed at a second resolution level, the second resolution level being finer than the first resolution level.

10. The method of claim 1 wherein the signal representing data from inspection of the test piece is a non-periodic signal.

11. An automated, computer-implemented method for detecting a physical feature of a test piece by detecting a pattern in a signal representing data from inspection of the test piece, comprising the steps of:

measuring a physical parameter of the test piece;

generating a digital point-ordered signal representative of the measured physical parameter;

generating a morphologically filtered signal from the digital point-ordered signal;

generating a baseline signal from the morphologically filtered signal, the baseline signal comprising a coarse resolution behavior of the digital point-ordered signal relative to the background noise signal and the peaks/troughs signal;

generating a background noise signal from the baseline signal and the digital point-ordered signal, the background noise signal comprising fine resolution behavior of the digital point-ordered signal relative to the baseline signal and the peaks/troughs signal;

generating a peaks/troughs signal from the baseline signal, the background noise signal and the digital point-ordered signal the peaks/troughs signal comprising intermediate resolution behavior of the digital point-ordered signal relative to the baseline signal and the background noise signal;

locating peaks/troughs from the peaks/troughs signal; and outputting peaks/troughs information indicating the physical feature of the test piece.

12. In a test system comprising a test piece, means for measuring a physical parameter of the test piece and means for generating a digital point-ordered signal representative of the measured physical parameter, an apparatus for detecting signal information representing a physical feature of the test piece by detecting a pattern in the signal representative of the measured physical parameter, comprising:

means, coupled to the means for generating the digital point-ordered signal, for decomposing the digital point-ordered signal into a baseline signal, a background noise signal, and a peaks/troughs signal;

wherein the decomposing means comprises:

means, coupled to the means for generating the digital point-ordered signal, for generating a morphologically filtered signal from the digital point-ordered signal;

means, coupled to the morphological filtering means, for generating a baseline signal from the morphologically filtered signal;

means, coupled to the baseline signal generating means, for generating a background noise signal from the baseline signal and the digital point-ordered signal; and means, coupled to the background noise seal generating means, for generating a peaks/troughs component signal from the baseline signal, the background noise signal and the digital point-ordered signal;

means, coupled to the decomposing means, for locating peaks/troughs from the peaks/troughs signal; and means, coupled to the locating means, for outputting peaks/troughs information indicating the presence of physical features of the test piece.

13. The test system of claim 12, wherein the test piece is a mechanical object and the measured physical parameter is the acceleration at a location on the mechanical object.

14. The test system of claim 12, wherein the test piece is a metallic piece and the measured physical parameter is the impedance produced by electromagnetic probing of the metallic piece.

15. The test system of claim 12, wherein the test piece is a living organism and the measured physical parameter is the electrical activity within the living organism.

16. The system of claim 12, wherein the baseline signal comprises coarse resolution behavior of the digital point-ordered signal relative to the background noise signal and the peaks/troughs signal.

17. The system of claim 12, wherein the background noise signal comprises fine resolution behavior of the digital point-ordered signal relative to the baseline signal and the peaks/troughs signal.

18. The system of claim 12, wherein the peaks/troughs signal comprises intermediate resolution behavior of the digital point-ordered signal relative to the baseline signal and the background noise signal.

19. The system of claim 18, wherein the peaks/troughs component signal generating means generates a peaks/troughs component signal at a first resolution level and the system further comprises:

means for decomposing the peaks/troughs signal constructed at the first resolution level into a baseline signal, a background noise signal, and a peaks/troughs signal constructed at a second resolution level, the second resolution level being finer than the first resolution level.

20. In a test system comprising a test piece, means for measuring a physical parameter of the test piece and means for generating a digital point-ordered signal representative of the measured physical parameter, an apparatus for detecting a physical feature of the test piece by detecting a pattern in the signal representative of the measured physical parameter, comprising:

means, coupled to the means for generating the digital point-ordered signal, for generating a morphologically filtered signal from the digital point-ordered signal;

means, coupled to the morphological filtering means, for generating a baseline signal from the morphologically filtered signal, the baseline signal comprising coarse resolution behavior of the digital point-ordered signal relative to the background noise signal and the peaks/troughs signal;

means, coupled to the baseline signal generating means, generating a background noise signal from the baseline signal and the digital point-ordered signal, the background noise signal comprising fine resolution behavior of the digital point-ordered signal relative to the baseline signal and the peaks/troughs signal;

means, coupled to the background noise signal generating means, generating a peaks/trough signal from the baseline signal, the background noise signal and the digital point-ordered signal the peaks/troughs signal comprising intermediate resolution behavior of the digital point-ordered signal relative to the baseline signal and the background noise signal;

means, coupled to the peaks/trough component signal generating means, for locating peaks/troughs from the peaks/troughs signal; and means, coupled to the locating means, for outputting peaks/troughs information indicating the physical feature of the test piece.

21. The system of claim 20, wherein the peaks/troughs component signal generating means generates a peaks/troughs component signal at a first resolution level and the system further comprises:

means for decomposing the peaks/troughs signal constructed at the first resolution level into a baseline signal, a background noise signal, and a peaks/troughs signal constructed at a second resolution level, the second resolution level being finer than the first resolution level.

22. An automated, computer-implemented method for detecting a physical feature of a test piece by detecting a pattern in a signal representing data from inspection of the test piece, comprising the steps of:

measuring a physical parameter of the test piece;

generating a digital point-ordered signal representative of the measured physical parameter;

decomposing the digital point-ordered signal into a baseline signal, a background noise signal, and a peaks/troughs signal;

wherein the decomposing step comprises the steps of:

generating a morphologically filtered signal from the digital point-ordered signal;

generating a baseline signal from the morphologically filtered signal;

generating a background noise signal from the baseline signal and the digital point-ordered signal; and generating a peaks/troughs signal from the baseline signal, the background noise signal and the digital point-ordered signal;

locating peaks/troughs from the peaks/troughs signal; and outputting peaks/troughs information identifying those signal patterns that indicate the presence of physical features of the test piece.

* * * * *